United States Patent [19]

Smallwood et al.

[11] Patent Number: 5,047,953
[45] Date of Patent: Sep. 10, 1991

[54] AUGMENTIVE COMMUNICATIONS SYSTEM AND METHOD

[75] Inventors: John M. Smallwood; William A. Custer, both of Northville, Mich.

[73] Assignee: Detroit Institute of Children, Detroit, Mich.

[21] Appl. No.: 387,961

[22] Filed: Jul. 31, 1989

[51] Int. Cl.$^5$ .............................................. G10L 5/00
[52] U.S. Cl. ................................. 364/513.5; 364/419; 381/51
[58] Field of Search ........................... 364/513.5, 419; 381/51–53

[56] References Cited

U.S. PATENT DOCUMENTS 4,661,916 4/1987 Baker .................................... 381/52

OTHER PUBLICATIONS

AI for Special Needs–and "Intelligent" Communication Aids for Bliss Users, Applied Artificial Intelligence, 1987.
The Don Johnston Developmental Equipment, Inc. (Catalog, 1988, 2 pages).
ComputAbility-The Handicapped's Source, Brochure, (2 pages).
The Wayne County Intermediate School District memo, "Wolf" (5 pages).
TechnicalAids and Systems for the Handicapped, Inc. (TASH), Brochure, (3 pages, 1987).
Zygo brochure, (6 pages, 1987).
Prentke Romich Company, Brochure (3 pages, 1988).
Adaptive Communication Systems, Inc., Brochure (3 pages).

Primary Examiner—Emanuel S. Kemeny
Attorney, Agent, or Firm—Harness, Dickey & Pierce

[57] ABSTRACT

An augmentive communications system ("ACS") and method for enabling handicapped individuals to generate sentences and also to control external devices. The ACS may employ auditory or visual feedback to present category and word choices to the user. With a single switch the user may select categories and words from these choices which then are stored in an input buffer to permit the construction of sentences. Alternatively, the user may select choices which permit the control of external devices such as a wheelchair by manipulating the single switch. The microprocessor controlled ACS system incorporates a simplified programming language and interpreter to permit nonprogrammers to construct user programs that are tailored to the particular needs of the individual user. In addition, as the user gains proficiency in using the ACS, the user program can be easily revised to permit more efficient and sophisticated communications.

14 Claims, 5 Drawing Sheets

Microfiche Appendix Included
(2 Microfiche, 159 Pages)

AUGMENTIVE COMMUNICATIONS SYSTEM AND METHOD

MICROFICHE APPENDIX

This specification includes a microfiche appendix having 2 microfiche with a total of 159 frames. This microfiche appendix, which constitutes part of the disclosure of this patent document, contains material which is subject to copyright protection. The copyright owner has no objection to the facsimile reproduction by anyone of the patent document or the patent disclosure, as it appears in the Patent and Trademark Office patent file or records, but otherwise reserves all copyright rights whatsoever.

FIELD OF THE INVENTION

The present invention relates in general to systems and methods for enabling handicapped individuals to communicate, and in particular to such systems and methods for enabling handicapped individuals to communicate by manipulating a single switch.

BACKGROUND OF THE INVENTION

Handicapped individuals frequently require assistance in areas such as communication, mobility, eating and play. This assistance is typically provided by persons such as therapists. Recent technological advances have resulted in communication devices and systems which give handicapped individuals a greater degree of independence and skill development than had heretofore been possible. Communication aids for nonverbal persons typically rely on the visual skills of the user for operation. One example of an early communication system was developed for use by nonverbal physically handicapped persons by C. K. Bliss in the 1930's. The Bliss system is based on a set of visual-pictorial symbols comprising four hundred symbols accompanied by appropriate English words, which are pointed to by the user. See Galliers, "A.I. For Special Needs-An "Intelligent" Communication Aid for Bliss Users", 1 Applied Artificial Intelligence 77 (1987). Frequently, however, such systems require visual or motor skills that are beyond the capability of the multi-handicapped individual. For example, a handicapped individual may not have the requisite motor skills to operate the computer keyboard required in some systems. In other cases, an individual may not have the requisite visual skills required to operate the system. For example, in some scanning systems the user watches a light or row scanning system until it reaches a specific spot, and the user must then activate a switch to operate speech output at that point. Persons with visual perceptual difficulties such as poor visual attending, visual tracking, visual scanning, etc. frequently have difficulties with these kinds of systems.

To overcome this problem, communication systems have been developed which do not rely on the visual skills of the user, but instead present information to the user auditorially. Such systems could then be used by persons with low visual functioning or even by blind persons. One system, known as the Audio Com, was developed by John Smallwood of the Communication Enhancement Resource Center of the Northwood Public Schools in Northville, Michigan. The Audio Com system utilized a Z80 single board microprocessor together with a Votrax "type and talk" system modified for battery operation. The Audio Com used a single switch input along with an earphone and an external speaker under the control of the software. Programming was done in BASIC. The user of the Audio Com could select words desired to be spoken from those stored in memory in the following way. The user would make momentary contact of a single switch which would cause the generation of a vocabulary category list from which the user could select a category he/she was interested in. These categories might be, for example, nouns, verbs, pre-stored phrases, and a selected number of subject categories, such as food, clothing, health care needs, or numbers. As this list of categories was being spoken by the Audio Com in the earphone, the user would actuate the switch for the category he wanted as that category was being spoken.

Next, the Audio Com would present entries from the selected category in sequential fashion allowing for a similar selection to be made by the user as the entry within the selected category was spoken. The Audio Com would then return to and repeat the category list so that another category selection could be made. This step of listing entries in the selected category was repeated again so that additional words or phrases could be selected. The selected entries were stored sequentially in a text buffer. This process was then repeated until a desired thought or message had been accumulated in the text buffer. To play out the text buffer upon completion of formation of the message, the user would hold a single switch closed for a longer than normal time (two or three times longer) such as 1.5 seconds. This put the Audio Com into a user command mode, at which time the speak function could be selected. In the command mode, the Audio Com would repeat a series of commands and the user would strike the switch at the time the desired command was heard. Commands being spoken included: backspace, clear and speak. The speak command spoke the text in the buffer, not through the user earphone, but through the external speaker so that another person could hear it. The Audio Com system also permitted the user to control relays which in turn provided single switch, on and off instructions to external devices. For example, four relay contacts would be used to move a wheelchair in four directions. Alternatively, the relays may be used to operate a Windsford automatic mechanical feeder, or other devices.

One disadvantage with systems such as the Audio Com is the length of time it takes for an individual to scan the required categories and list of words in order to construct useful phrases. Because of this limitation, programming the Audio Com resulted in a compromise between available vocabulary and speed. That is, as the potential vocabulary increases the number of categories and word choices must increase, and this slows down the phrase building task of the user. Phrase building can be streamlined by reducing the number of categories and words, however, this limits the available vocabulary. Thus, it would be desirable to provide a method for streamlining the process of constructing phrases without limiting the available vocabulary.

Another problem with the Audio Com system is that it is not easily adaptable to the particular needs and capabilities of the user. By the same token, the Audio Com system was not easy to upgrade to the increasing level of proficiency of particular users. This is because the software for the Audio Com system was written in BASIC and program changes could only be performed by persons with the necessary programming skills, and who also understood the systematic rules relative to the construction of words using phonemes for the Votrax speech system. As a result, therapists, who were in the best position to understand the individual needs of the user, were unable to adapt or customize these programs to particular users since they were typically neither computer programmers nor familiar with the nuances of generating suitable command words for driving a votrax speech synthesizer. Consequently, it would be desirable to have a communication system in which therapists and other non-programmers can easily change the categories and word choices to better match the abilities and interests of each individual user.

In light of the foregoing problems and needs, it is an object of the present invention to provide new methods and systems for enabling multi-handicapped nonverbal individuals to interact with persons and systems. It is another object of the present invention to provide methods and systems for single switch generation of synthetic speech and other communications in which sentences can be constructed in a quicker and more streamlined fashion without limiting the available vocabulary. It is a further object of the present invention to provide a communication system which is easily adapted to the individual needs and abilities of the user. Still another object of the present invention is to provide a communication system which utilizes a simplified programming method so that persons who are not computer programmers can modify the language capability of the system to match that of the user.

SUMMARY OF THE INVENTION

In light of the foregoing objects, there is provided, according to the present invention, an augmentive communication system (ACS) which uses an interpreter and a very simplified programming language so that any therapist familiar with the system, even though not a programmer, can realize a wide variety of functions. These functions permit modifying the language capability, by such techniques as deleting or adding words and phrases, and by restructuring the order of the available menu. Also, the ACS has the ability to provide automatic branching functions in connection with selected sentence fragments.

To enable a user to construct sentences, the ACS presents the user with categories of words and phrases from which to choose. When the user actuates a single switch within a predetermined interval of time after the category is presented, the ACS will scroll through the individual words which are programmed into that category. When the user selects one of these individual words by activating the switch, the ACS will then either speak this word or store this word in an input buffer and again present the user with the categories from which to choose. By selecting and storing words, the user can build complete sentences in the input buffer until it is desired to present them to persons other than the user.

Specific users often have a unique combination of handicaps, and the ACS may be tailored to fit these individual needs and capabilities. For example, the single switch may be adapted to match the user's motor capabilities. Or, the method of presenting the choices may be tailored to match the user's capabilities, for example, by choosing visual or audio input.

The present invention has several aspects, the more important of which will now be summarized. According to a first aspect of the invention, there is provided in a programmable system for enabling a user to generate sentences from a set of stored words and phrases by actuating a single switch in response to choices presented to the user, a method of generating sentences. This method comprises the steps of: storing in the programmable system at least one set of instructions executable by the system, which defines the choices and their order of presentation, the set of instructions including individually numbered instructions, each having a first line number for identification, a command symbol, at least one word to be presented to the user as one of the choices, and at least one second line number for indicating which individual instruction to execute next; executing the instructions in said system by: (a) locating a first individual instruction to be executed from the set of instructions; (b) determining if there is more than one second line number in the instruction to be executed; (c) when there is no more than one second line number in the instruction to be executed, executing the function defined by the command symbol of the instruction to be executed, and proceeding to the individual instruction indicated by the second line number designated in the instruction to be executed; (d) when there is more than one second line number in the instruction to be executed, presenting a word in the individual instruction indicated by the first such second line number to said user; (e) determining if said single switch has been actuated within a predetermined interval of time after said word is presented to said user; (f) when said switch is actuated within said predetermined interval of time, executing said function defined by said command symbol in the individual instruction indicated by the first such second line number in the instruction to be executed, and proceeding to the next second line number designated in the instruction to be executed; (g) when said switch is not activated within said predetermined interval of time, presenting to said user a word in another individual instruction indicated by the next second line number in the instruction to be executed; (h) repeating steps (e), (f), and (g) for each successive second line number listed in the instruction to be executed.

According to a second aspect of the present invention, there is provided a programmable system for enabling a user to generate sentences from stored words and phrases by actuating a single switch in response to choices presented by the user, according to the method described above. This system is preferably microcomputer based, and will be described in detail shortly.

These and other aspects, objects and advantages of the present invention will be better understood by reading the following detailed description in conjunction with the accompanying drawings and appended claims.

BRIEF DESCRIPTION OF THE DRAWINGS

The drawings form an integral part of the description of the preferred embodiments and are to be read in conjunction therewith. Like reference numerals designate like components in the different figures, where.

DETAILED DESCRIPTION OF THE PREFERRED EMBODIMENTS

A. SYSTEM OVERVIEW

Figure 1:
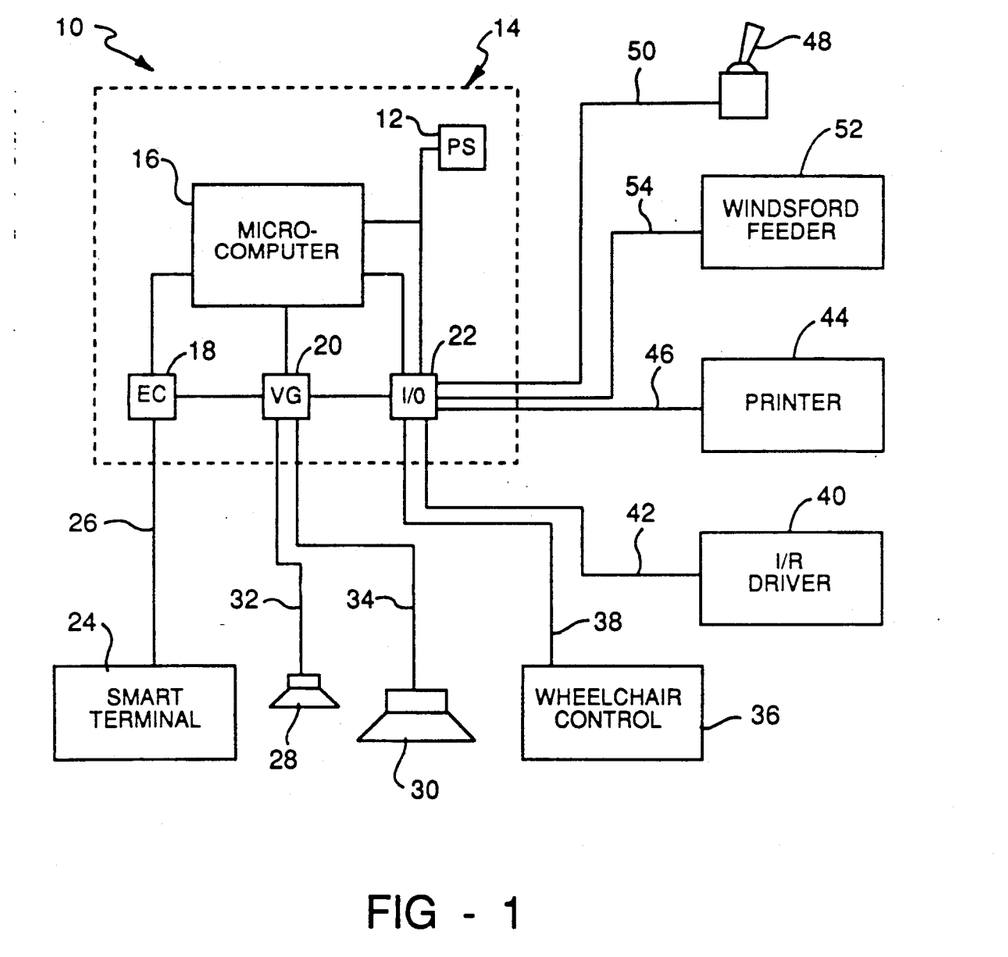
FIG. 1 is an overall functional block diagram of the augmentive communication system ("ACS") in accordance With the present invention.

In FIG. 1 there is shown a functional block diagram of the augmentive communication system (ACS) in accordance with the present invention. The ACS is designated generally by reference numeral 10. Power to the ACS is provided by a power module 12 which preferably supplies power to the ACS 10 by means of a battery so that the ACS is portable. The ACS 10 is controlled by the system hardware 14 which includes the power supply (P/S) module 12, a microcomputer 16, an external communications (EC) module 18, a voice generation (VG) module 20 and an input/output I/0 module 22. The components of the hardware system 14 will be described in more detail below. Hardware system 14 is portable and may easily be incorporated into a carrying case or attached to a wheelchair. Programs are entered in the ACS 10 by means of a smart terminal 24 which may be, for example, an IBM personal computer or an Apple computer, such as an Apple II E with dual floppy disk drives. The smart terminal 24 is connected to the hardware system 14 by means of an RS232 bus 26.

Also, included in the ACS 10 is a pair of audio speakers 28 and 30. Speaker 28 is a private speaker which may be, for example, a pillow speaker mounted near the head of the user. Speaker 30 is a larger public speaker which may include additional amplification so that it may be heard easily by persons other than the user. Speakers 28 and 30 are attached to the hardware system 14 by means of audio conductors 32 and 34. A wheelchair interface 36 is provided for controlling the operation of a wheelchair and is attached to the hardware system 14 by means of conductors 38. Also optionally included in the ACS system is an infrared (IR) driver 40 for controlling infrared remote devices that may permit the control of appliances such as televisions and stereo equipment. A conventional infrared driver 40 is connected to the hardware system 14 by means of connector 42. A printer 44 may also provided which is connected to the hardware system 14 through bus 46. A switch 48 is connected to the hardware system 14 by means of conductor 50. A conventional Windsford feeder 52 is also shown in FIG. 1, and may also be connected to the hardware system 14 by means of conductor 54.

In operation, the ACS 10 is programmed through the smart terminal 24. Two types of software will generally be required: an operating system may include one or more programs, which may be written in a conventional programming language such as assembler or BASIC; and application software which will include at least one user program, which will preferably be written in the threaded simplified language instruction ("TSLI") language in accordance with the present invention. These programs are described in more detail in connection with FIGS. 4-6. A number of the routines or programs forming part of the operating system are strictly conventional in the microcomputer design art, such as the boot-up program used to initialize the system when first turned on, the RS232 driver routine, and the like, and thus need not be described here. The operating system also includes an interpreter program for interpreting and executing the user program in TSLI. While the creation and the operating system requires certain conventional programming skills, the designing, writing and alteration of user programs in TSLI can easily be performed by non-programmers, such as therapists, who are working with the users. In this way, a therapist familiar with the capabilities of the particular user can easily construct a user program that is tailored to the capabilities of that user. It will be appreciated that a user program customized in this way will optimize the user's ability to construct sentences and control external devices.

The ACS 10 has two basic modes of operation: a "program" mode which allows the ACS 10 to be programmed by a therapist or other person; and a "scan" (or "user") mode, where the ACS 10 runs the user program which has been entered into it. Details of the operation of both modes are provided later. Once the operating system and user programs are entered into the microcomputer 16 by downloading them through the smart terminal 24 when the ACS 10 is in the program mode, the smart terminal 24 can be disconnected from the hardware system 14, since it is no longer required to enable the user to operate the ACS 10 in the user mode. To turn on the ACS 10 in either mode, the user first actuates the switch 48. This switch may be a conventional lever or joy stick type switch, or it may be any one of a number of other types of switches, adapted to the preferences and capabilities of the user. For instance, actuation of the switch does not have to be by the user's hand, but instead, switch 48 could be adapted to be actuated by other means such as the user's arm, foot or head etc. Once the ACS 10 is turned on the user will be presented with categories of words and phrases. This presentation may be through private speaker 28 mounted near the user for those who are able to hear and process verbal speech. Alternatively, the presentation of words and categories may be through a printer 44 or other visual display means for users who are better able or may only be able to see and process visual information.

The categories that are presented to the user, may include categories of words for constructing sentences, or categories of commands for external controllable devices such as wheelchair controls 36, the Windsford feeder control 52 or the IR driver control 40. Immediately after the user hears the category that he is interested in he again actuates the switch 48 to select that category. (By "actuating the switch" it is meant that the user depresses the switch momentarily and then releases it.) This will cause the microcomputer system 16 to present an additional list of choices pertinent to only the selected category. Where the user chooses a mobility category for controlling the wheelchair, for example, the user may then be presented with wheelchair control options such as forward, back, left and right. When the user is presented the choice he desires he again immediately actuates switch 48 and, depending on the mode of operation, this may immediately activate movement of the wheelchair. Wheelchair movement may then be stopped when the user activates the switch again.

Alternatively, where the user chooses a category of words, the ACS 10 may then present a list of words within that category. The choice of an individual word may cause the microcomputer system 16 to store the choice in an input buffer. The user would then be presented with additional choices of categories which would permit the user to construct individual phrases and sentences in the input buffer.

When the switch 48 is held depressed for a longer than normal than time period of time, for example one and a half seconds, the microcomputer system 16 will enter a command mode. It will be appreciated that other ways to activate the command mode may be utilized. For example, the microcomputer system 16 may instead be programmed to recognize, not a longer actuation of the switch 48, but two rapid actuations of switch 48 closely spaced in time. In any event, when the microcomputer system is placed in the command mode, the user will then be presented with command options. The command options, which will be explained in more detail below, may permit, for example, the user to listen to the content of the input buffer through the private audio speaker 28 or the public speaker 30 as desired, or may permit editing of the content of the input buffer.

B. HARDWARE SYSTEM

Figure 2:
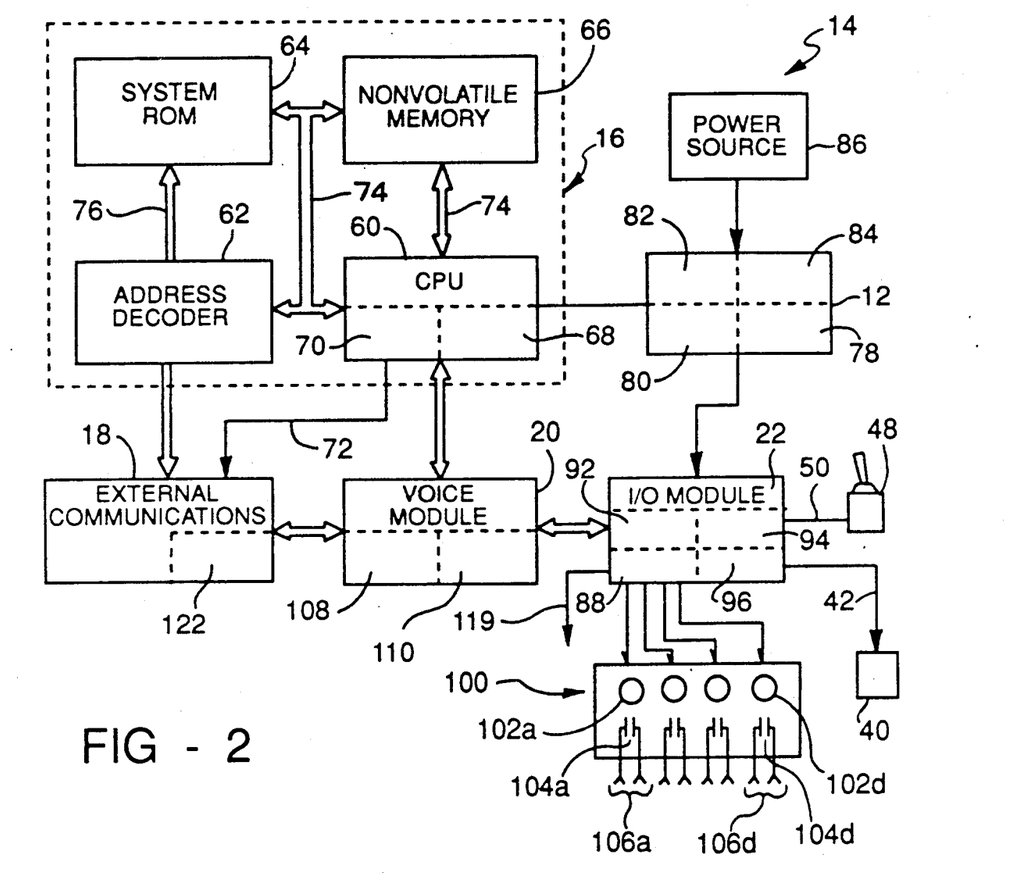
FIG. 2 is a detailed block diagram of the hardware system of the present invention illustrating its internal architecture controllers /buffers and I/0 modules.

FIG. 2 shows in block diagram form a preferred embodiment of the microprocessor based hardware system 14 of the present invention. The hardware system 14 includes the following main blocks: a central processing unit (CPU) module 60, the power supply module 12, the I/0 module 22, a voice generation module 20, an external communications module 18, and three further blocks 62, 64 and 66 which are used in conjunction with the CPU module 60 to form a microcomputer system 16.

The CPU module 60 in the preferred embodiment is implemented with a Zilog Z80 CMOS microprocessor chip which is driven by an Intersil Model No. 7209 clock oscillator integrated circuit (IC), which provides a 2.44 MHz system clock signal. The output of the 7209 IC 68 is provided to a standard divider circuit IC chip 70, which may be an RCA model 4040 in order to provide a second slower clock signal on line 72 at 19.2 KHz to run components within I/0 module 18, as will be explained later. Blocks 62, 64 and 66 within microcomputer 16 are respectively an address/decoder, system read only memory (ROM), and nonvolatile storage such as a Dallas Semiconductor Model No. DS 1225 8K EPROM. The interconnections 74 between the CPU 60 and blocks 62, 64 and 66 are of conventional design and include data lines, address lines and conventional control lines for conventional handshaking functions (such as input/output, memory requests, etc.). Chip select lines 76 extend in conventional fashion between address decoder 62 and system ROM 64. Upon selection of desired ROM locations in block 64, suitable address and data information is output from block 64 via address-/data lines 74 to RAM in block 66, for use by the microprocessor during a subsequent instruction cycle, as is well understood by those skilled in the art of designing microcomputer based systems.

The power module 12 is also of conventional design and includes a power-on reset chip 78 such as a Dallas Semiconductor Model No. DS1231, a low voltage detector chip 80 such as Intersil Model No. 8211, a conventional 5 volt regulator chip 82 such as an L.P. 2905, and a conventional magnetic latching relay 84 to turn the DC power on and off to the remainder of the modules within the hardware system 14. A portable power source 86 of conventional design utilizing batteries is also provided, which permit the ACS 10 to be portable.

The remaining three modules 18, 20 and 22 are used to implement all input/output functions from the microcomputer 16 to the rest of the world. The I/0 module 22 includes a relay driver chip 88, a system output chip 92, a system input chip 94 which may respectively be a Sprague Model No. ULM2803, a Motorola Model No. 74HC373 and a Motorola Model No. 74HC244. Optionally, a programmable peripheral interface chip 96, which may be an Intel Model No. 8255, may also be provided for driving external circuitry, as will be further explained. The relay driver 88 is used in the augmentive communication system 10 of the present invention as the driver of a group 100 of relay coils 102a–102d, which each respectively have associated therewith one of the normally open contacts 104a–104d. Independent pairs of conductors 106a–106d are wired to each of the relay contacts 104a–104d to provide electrical isolation so that these relay contacts can be used to separately drive external devices such as a wheelchair control 36 or a Windsford feeder 52, as will be further explained. For convenience, in the user program, the contacts 104a–104d are referred to as the "W", "X", "Y" and "Z" contacts or switches.

Figure 3:
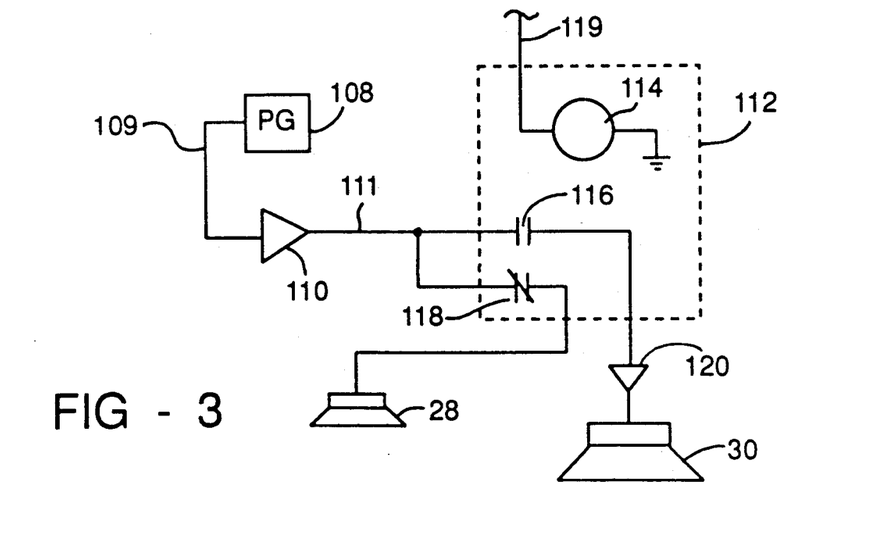
FIG. 3 is a circuit diagram illustrating in detail the voice module shown in FIG. 2.

The voice module 20 in the preferred embodiment of hardware system 14 includes a phoneme generator IC chip 108, such as a Model No. SC01 chip available from Votrax, Inc. of Troy, Michigan. The phoneme-based generator (PG) 108 provides an analog output signal to a linear amplifier 110, such as a Motorola Model No. LM386. As shown in detail in FIG. 3, the linear amplifier 110 receives the analog signal produced by the phoneme generator 108 on line 109. The linear amplifier 110 then amplifies this weak analog signal up to a suitable level on line 111 before the amplified signal is delivered to a relay module 112. The relay module 112 includes a relay coil 114 which operates a pair of contacts 116 and 118 which are respectively shown as normally opened and normally closed. The relay coil 114 is driven by the relay driver chip 88 located within the I/0 module 22 via line 119. When the relay 114 is de-energized, the normally closed contact 118 is closed, this allowing the signal on line 111 to pass to a small private speaker 28 located adjacent to the user's ear. When the relay coil 114 is energized, contact 118 is open and contact 116 is closed, thereby allowing the amplified signal on line 111 to pass to a public speaker 30 which may be several times the size of private speaker 28 and may include additional amplifier 120 so that the amplified signal on line 111 may be heard by listeners in the same general area as the user of the ACS system 10.

The external communications module 18 is provided to enable the microcomputer 16 to communicate with other computers or computer-related communication devices such as a personal computer. Alternatively, the communications module 18 could be set up to communicate with a printer or modem. The communications module 18 is of conventional design and may include, for example, a Zilog serial input/output UART chip 122.

The Windsford feeder 52 is driven by two signals which may be, for example, from two of the relays 102a–102d. The first relay will control the rotation of a plate on a turnstile, and the second will control the "one direction-only" motion of the mechanical arm which may have a conventional spoon/scoop on the end thereof. The ACS 10 has made the Windsford feeder computer controlled and allows for adjustable plate spin and scoop cycle. By using the automatic repeat functions of the suitable TSLI program, an automatic feed cycle can be programmed by the the rapist. The user pause command causes a wait state, holding existing conditions, for the number of seconds specified.

The WC command is used to cause the first relay to close, while the WO command causes the first relay to open. An adjustable on time for the relay is achieved by use of a WC, U and WO command sequence which turns on the relay for the number of seconds specified by the U command. In this manner the motor driving the Windsford turnstile can be pulsed to provide a slower than otherwise possible rotation of the plate.

C. ACS INSTRUCTION SET

1. Operating System Commands

The ACS user uses two kinds of programs, an operating system command program and a user program. In the preferred embodiment, the operating system command program uses a conventional commercially available telecommunications package loaded on the smart terminal 24, shown in FIG. 1, to enter application programs and to make changes in both the operating system commands and the user program. It will be appreciated that a dumb terminal may also be used, but additional commands will then be incorporated into the operating system program, as discussed below.

Figure 4:
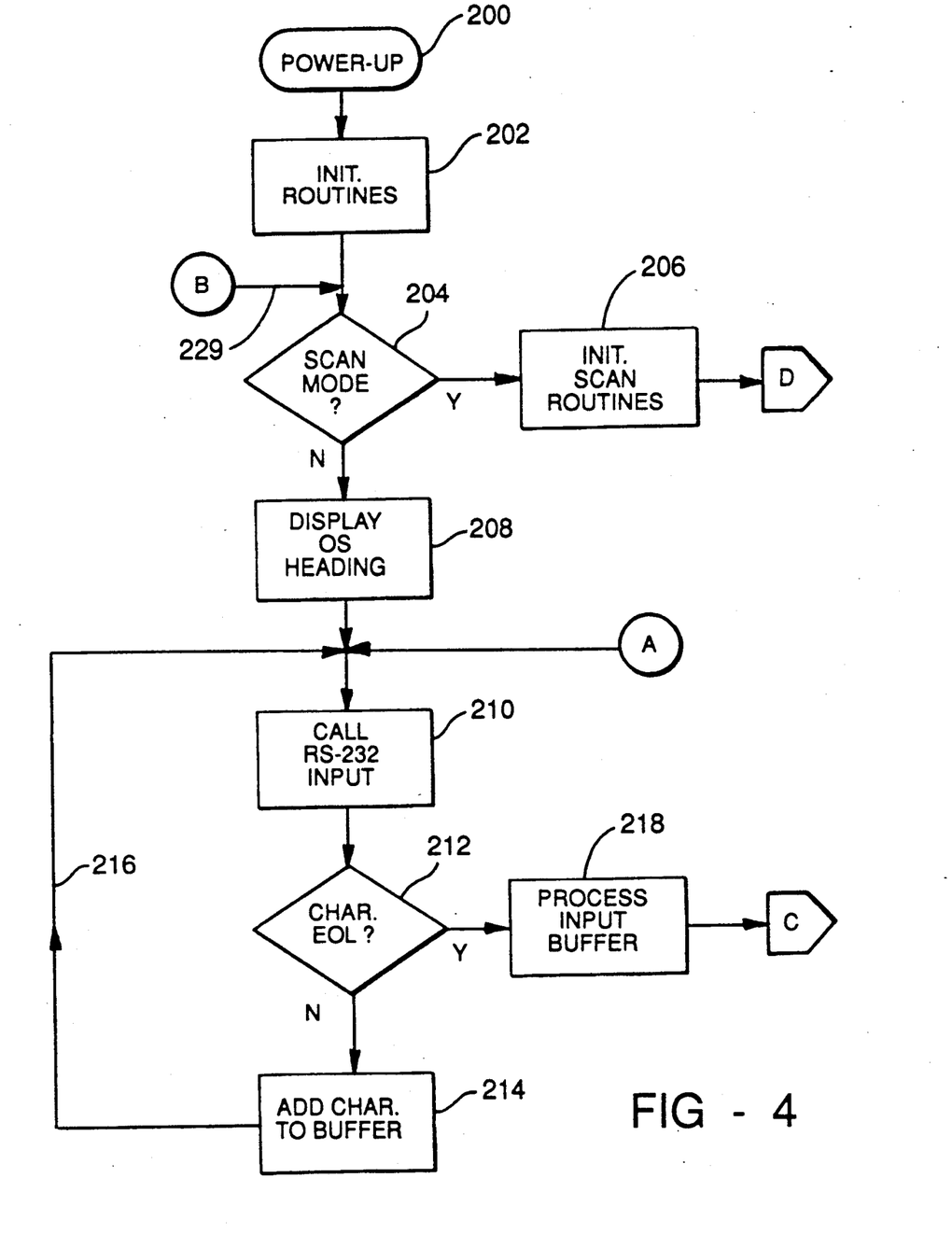
FIG. 4 is a software flowchart of the operating system of the ACS of FIG. 1.
Figure 5:
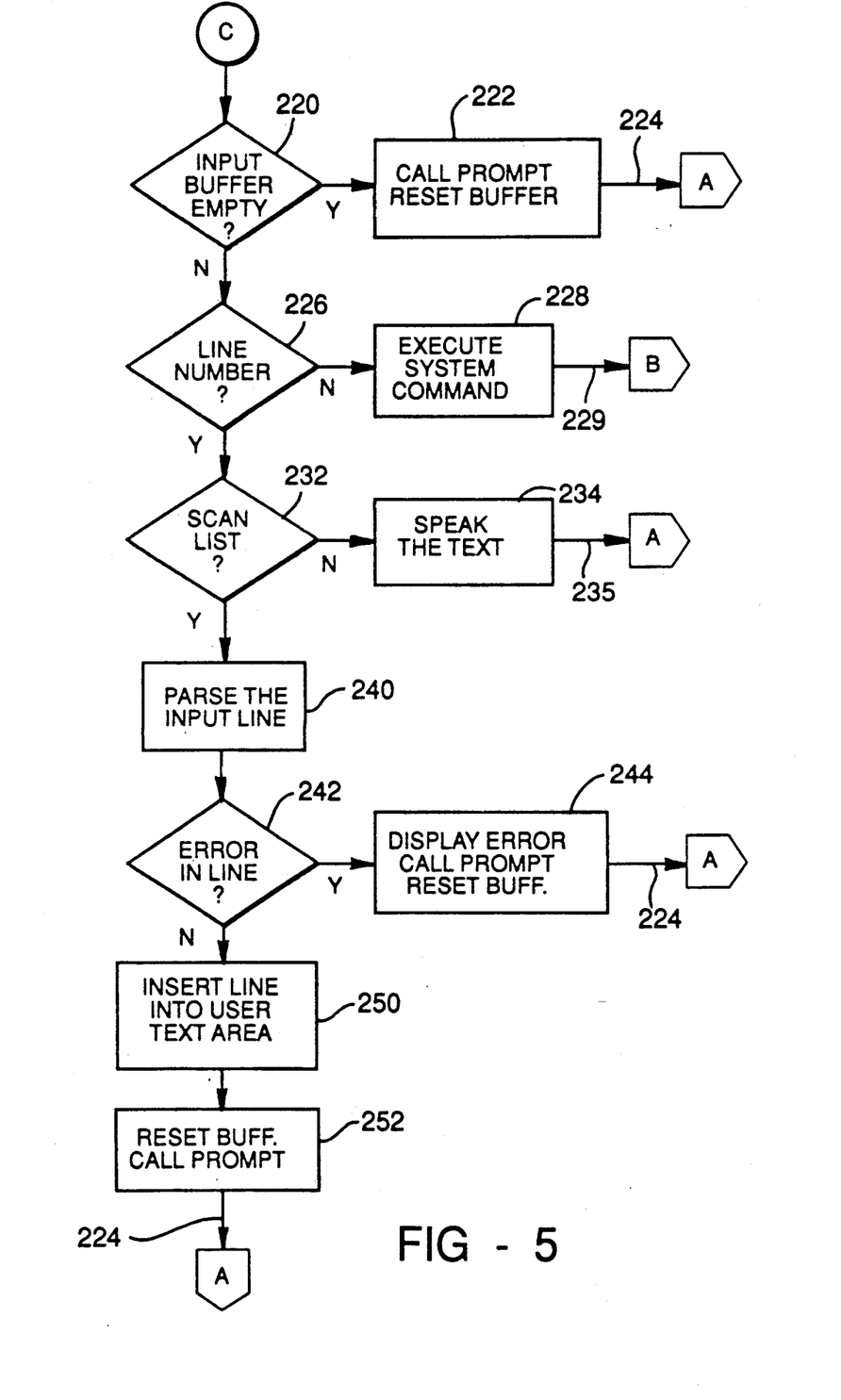
FIG. 5 is a software flowchart of the routines used to process the input buffer in the FIG. 4 program.
Figure 6:
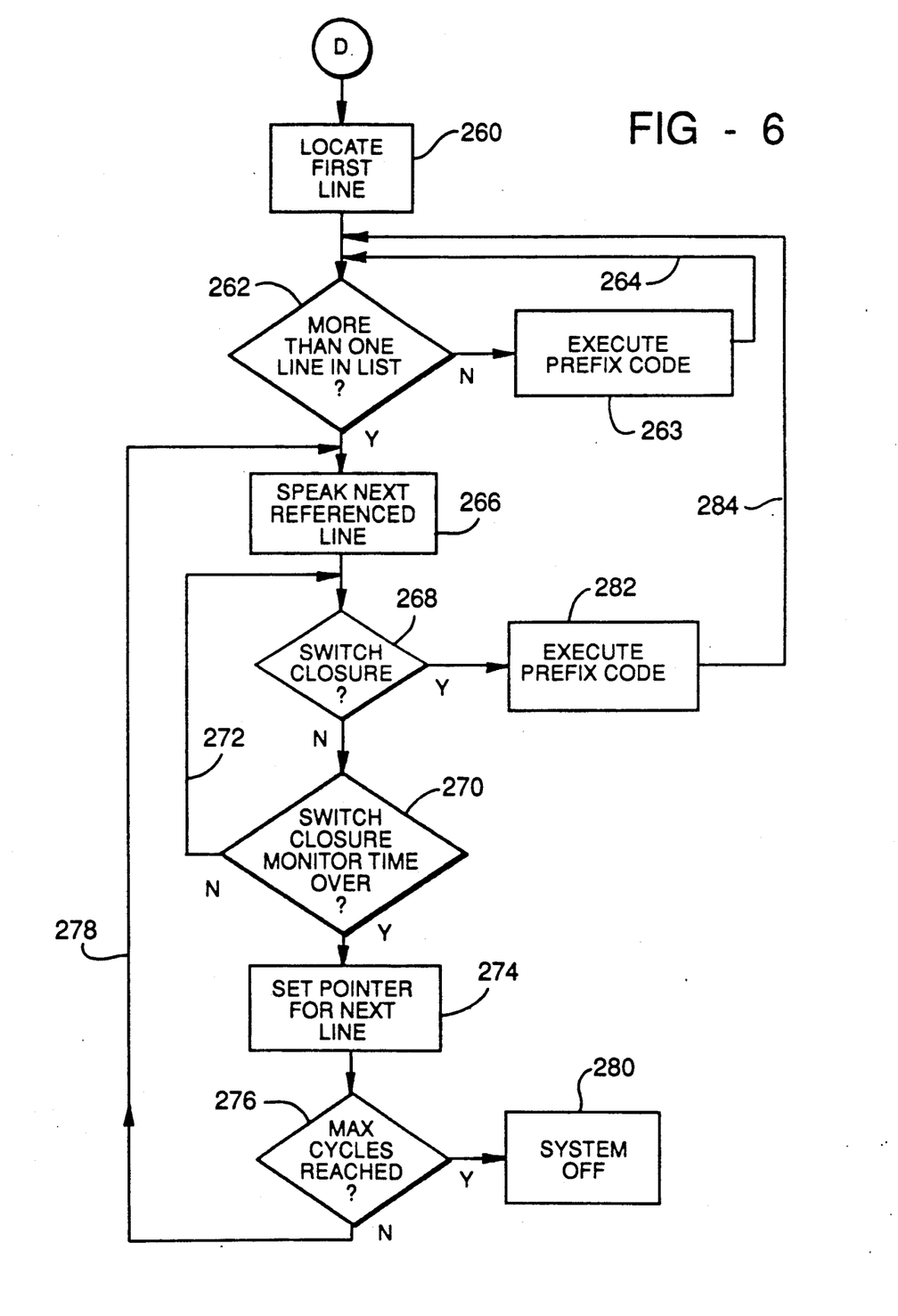
FIG. 6 is a software flowchart of the "scan" routine of the program shown in FIG. 4.

Software flowcharts for the operating system command program and the user program are shown in FIGS. 4-6 and will be described in more detail below. Also, a listing of the operating system program is contained on the above-referenced microfiche appendix. This appendix contains programs and files for the following functions: operating system, interpreter, and text-to-phoneme program and the phoneme codes used by this last program. First, the operating system commands and the user program commands will be described. These commands may be used to adapt the operation of the ACS to the particular needs of a given user. These commands may be easily changed by a therapist to suit the needs of different users.

AUTO=(2-255). The AUTO command sets the number of times the ACS will cycle through a list of choices presented to the user before causing an automatic off. This saves battery power if the system is turned on accidentally. This value may be set from 2 to 255 cycles. For example, if AUTO is set to 5 the system will shut down after 5 cycles through any menu without a switch closure.

DUPLICATE=(Y.N). The DUPLICATE command will either allow or not allow the user to select the same vocabulary item twice in a row. Some individuals have a tendency to "stutter" while using a communication aid. For example: I WANT WANT TO GO GO HOME. By using the command DUP=N the system will not allow the second selection of WANT or GO. Instead, the system will say "CANCEL" when the second duplicate selection is made.

FEEDBACK=(Y,N). The FEEDBACK command, when set to "Y", will cause an echo of the message buffer after each selection of a vocabulary item. This feature will help remind the user what he or she has done so far.

HOLD=(Y.N). The HOLD command will cause the computer to wait for a switch closure from the user after the execution of the SPEAK command or a SPEAK IMMEDIATE selection. This mode is turned on by typing "HOLD=Y". The default value of HOLD is the "NO" condition.

INTERRUPT=(Y,N). The INTERRUPT command will enable or disable the system from jumping to the second line in the program upon holding the switch closed for a specified period of time. This is very useful for most users. It allows the therapist to place frequently used items and commands in one menu defined on the second line in the program text. INTERRUPT=Y will then allow the user to hold the switch closed for a period of time set by the WAIT command until he hears that item or menu spoken. Releasing the switch at this point will start the scan.

LIST or (line#-line#) or (line#-). The LIST command will list the lines of the program text. LIST will list all the lines, LIST 100-500 will list all lines starting with 100 through 500. LIST 100- will list all lines starting at 100 and ending with the last line of the program.

NEW. The NEW command will erase all of the program lines that make up the vocabulary.

OFF. The OFF command will turn the system off. This is useful since even during the programming phase, the ACS 10 is running on batteries.

QUERY. The QUERY command will list the current state of the machine settings. For example, typing of QUERY may cause the following:

| | | |
|---|---|---|
| AUTO=10 | SCAN=20 | TIME=20 |
| WAIT=20 | | |
| DUPS=Y | FEEDBACK=N | HOLD=N |
| INT=N | VETO=N | |

RUN. The RUN command will cause the microcomputer 16 to start executing the vocabulary in the scan mode. This execution will always begin with the first line in the program text. If the "A" key on the external programming terminal 24 is depressed, it interrupts the scan and returns the microcomputer 16 to the programming mode.

If the "RUN" command is typed, and then the system 10 is turned off manually and the external computer disconnected, the system 10 will function autonomously in a stand-alone mode.

SCAN=(1-255). This command sets the speed of the auditory scan. By increasing the number value (i.e., SCAN=50) the time allowed for switch selection between items is increased. Each digit represents approximately 0.05 seconds, so that, for example, SCAN 26 represents 1.30 seconds, and SCAN=27 represents 1.35 seconds.

TIME=(1-255). This command sets the amount of time allowed for the user to veto or, in other words, override his or her selection. Each value is approximately 0.05 seconds and VETO=Y must be set. (See VETO command below).

VETO=(Y.N). This command will enable/disable the veto or user override. If VETO=Y then when the user closes the switch the system 10 will produce an "ew" sound that will continue for the amount of time specified by the TIME command. Pressing the switch during the "ew" sound will cancel the selection. If the switch is not pressed during the "ew" sound the system will treat the selection as valid.

WAIT=(1-255). This command sets the amount of time that the switch must be held closed to invoke the interrupt function (see the INTERRUPT command).

Another set of ACS commands are necessary to run, stop or view on the monitor individual programs. These include:

R. "R" is the run command. After a database has been sent to the ACS, typing "R" will cause the auditory scroll to begin.

A. "A" performs an "abort" function by cancelling out the "run" mode. When a database is running the ACS, typing "A" aborts the run mode, stopping the auditory scanning. However, that database is still in the memory and has not yet been cleared.

NEW Typing "NEW" after a database has been aborted erases it from the memory in the ACS. The ACS is then ready to receive a different database.

L Inputting "L" will "list" a database which has been loaded and sent to the ACS; the "listing" appears on the computer monitor.

C Once a database has been programmed, but before it is saved to disk, a quick "check" procedure is conducted. After the final line of a program is typed, enter letter "C" followed by "RETURN". A "check" is completed to detect any line number errors; this however, does not identify all possible program errors. If errors are not detected, "OK-CHECK IS COMPLETE" is indicated on the monitor. If line number omissions are detected, these will be listed on the monitor.

It will be appreciated that additional conventional commands or functions may be necessary, and these may be performed by the smart terminal 24. Alternatively, when a dumb terminal is used, the operating system must be able to recognize these additional commands. Such conventional commands or functions might include, for example, one or more of the following activities:
sending a database from terminal 24 to the ACS 10;
printing a database;
writing a database to disk;
copying a database to the smart terminal's buffer;
clearing the smart terminal's buffer;
viewing disk files;
viewing the smart terminal's buffer; and
performing disk commands (catalog or delete).
The software and hardware elements necessary to perform these commands and functions in a microcomputer system are very well known, and need not be further described here.

2. User Program Structure and Commands

The user program is written in a simplified language, called "Threaded Simplified Language Instructions" ("TSLI"). Its chief advantage is that it does not require any previous programming experience. With TSLI, non-programmers, such as therapists, can write user programs which are tailored to the particular needs of a given user. The user program is executed by the interpreter program as discussed below in connection with FIGS. 4-6. Another key advantage of TSLI is that it permits the therapist to write user programs which have automatic branching functions. For example where the user selects the phrase "I want to talk to ____," the interpreter automatically branches to the list of names pre-stored in memory and begins playing them out on the private speaker, thus facilitating rapid sentence formation and ease of use. A second example is the phrase "I want my ____," with the interpreter automatically branching to and speaking a list of personal possessions. A third example is "I want to go to ____," and the interpreter automatically branching to and speaking a list of places. Other examples are possible.

The TSLI syntax requires that each word, category, command, or phrase be contained on one line of text in the user program. Each text line begins with a line number field which accommodates line numbers in the range of 1-65535. The next field is for a letter prefix code, followed by a field for the correct spelling of the word to be spoken. The fourth field is for an optional spelling, followed by a colon and a scan list. For example:
1000 V,Alice; al liss:2000:3000:4000:5000

The 1000 locates the line, V is the prefix code for a vocabulary item, Alice is the correct spelling of the word to be presented, but the optional spelling of "al liss" is needed for proper pronunciation by the Votrax voice generation module 20. An example of a simple TSLI program is as follows:
1000 C,MENU:1010:1020:1030
1010 I,YES:1000
1020 I,NO:1000
1030 O,OFF;1000

When the system runs this program it will speak through the earphone the words Yes, No, Off. This is because the (C)ategory in 1000 has lines 1010,1020,1030 as its scan list. If the user were to press the switch after the word "yes" were spoken, the system will speak "YES" through the public speaker 30 because at line 1010 the (I)mmediate prefix code instructs the system to "speak immediately" the word on that line. Control is transferred back to line 1000 because it is the only line number in the scan list for line 1010.

This is a simple example of how the system works in conjunction with a TLSI user program. By adding more categories, words and commands a very complex and sophisticated communication system can be realized by a therapist or other person familiar with the operating system commands and TLSI language.

3. Definition of Prefix Code

Each line of the user program text should contain a prefix code that describes the vocabulary item in that line. For example:
1000 C,FOOD:1010:1020:1030:1040

The "C" in line 1000 indicates that FOOD is a category. When the ACS system 10 executes this line it will scan lines 1010, 1020, 1030, 1040 that can be programmed by the therapist to be items of food that comprise the "FOOD" category. The following example is of a different code.
2000 V,FOOD:2010:2020:2030:2040

The "V" indicates that FOOD is the word "food". When the user selects the word "food", the system executes line 2000 it will place food in the message buffer as part of a sentence. It will then scan lines 2010, 2020, 2030, 2040 which should be categories or items that logically follow the selection of the word "food".

Each of these prefix codes is independent of the word that is associated with it. If desired, any word could be used for example to direct the system 10 to turn off. This can be very useful for users that might not understand words like "backspace" or "clear". Instead, words like "oops" or "all done" can be used with the proper prefix codes. A list of all the prefix codes follows.

B-ackspace will instruct the system 10 to remove the last selection from the current message buffer. Attempting to "backspace" an empty buffer will not create any problems.

C-ategory will simply transfer control of the auditory scan to the list of lines that comprise the category. It is also useful in some situations to have a category of just one item. Control will automatically transfer to this line. One situation where this has proved useful is phrase programming for mnemonics. A mnemonic in the ACS 10 is deemed to be one word which represents an entire phrase to be spoken. For example, the word "bathroom" preceded by the "C" prefix means speak the phrase "I need to use the bathroom", which will be spoken by the ACS 10 if the word "bathroom" is selected by the user while scanning a category of such phrases. This is one example of phrase programming for mnemonics.

D-ump will erase the contents of the current message buffer.

I-mmediate will cause the system 10 to switch to the external speaker 30 and speak the line (most phrases are coded in this fashion).

L-isten will cause the current message buffer to be spoken through the user's private speaker 28. This allows the user to preview his or her communication.

O-ff will cause the system 10 to turn off the main power.

P-rint will cause the system 10 to print the contents of the message buffer through the printer 44.

S-peak will switch voice output to the public speaker 30 and then "speak" the current message buffer.

U-ser cause will cause the ACS 10 to wait "x" number of seconds before proceeding. The number of seconds "x" is specified as part of this prefix command. For example "U10" means pause ten seconds.

V-ocabulary is the word level of the ACS 10. Each item coded with the "V" code will be placed in the message buffer as part of a sentence. This is also the default code. If there is not a specified prefix code in a line of the program text, a "V" code will be assumed by the ACS system 10.

W will cause the system to turn on the "W" switch of the relay driver 88. The system 10 will continue to hold this line down until the switch 48 is depressed once again.

X will cause the system to turn on the "X" switch of the relay driver 88. The system 10 will continue to hold this line down until the switch 48 is depressed once again.

Y will cause the system to turn on the "Y" switch of the relay driver 88. The system 10 will continue to hold this line down until the switch 48 is depressed once again.

Z will cause the system 10 to turn on the "Z" switch of the relay driver 88. The system will continue to hold this line down until the switch 48 is depressed once again.

D. SOFTWARE ORGANIZATION

The operation of the ACS software when in the program mode is shown in the flow charts in FIGS. 5 and 6. In order to operate in program mode, the ACS 10 must be hooked up by the external communications module 18 to preferably a smart terminal 24. One advantage of a smart terminal over a dumb terminal is that with a smart terminal, such as a personal computer, the programmer can save the vocabulary that he or she is programming on a disk for future reference. The personal computer can save the program in whatever language is being utilized, as an ASCII file, for example. The ACS 10 saves the information being programmed into it in a compressed data mode in nonvolatile memory storage 66. The data compression technique involves: (1) compressing line number to two byte hexadecimal value (01 to 65,535), (2) removing the colons which act as delimiters in the lines of text; and (3) adding a value equal to the count or number of lines referenced in the scan vector. No other data compression techniques are utilized. Each line is stored as an individual record within the nonvolatile storage 66, which record may be as long as needed, up to 255 bytes. The first two bytes in the record are the line number, and the next byte is the length of the record expressed as a number of bytes including the two bytes taken for the line number. The fourth byte contains the prefix code (if any). The next group of bytes contains the orthography (the actual spelling of) the word in this line of text (if any), which field is ended with a semicolon. The next group of bytes contains the phonology of the word, that is the corrupted English spelling required by the Votrax Chip 108 in order to make the sound come out correctly per the Votrax pronunciation rules, which group is ended with a colon. The last field in the record is a string of line numbers in two byte representations which are in the scan vector of the line text.

Turning now to FIGS. 4 and 5 there is shown a flow charts detailing the sequence of operation of the operating system. The flow chart in FIG. 4 begins with the normal power up step 200 and initialization routines 202 which enables the system to check itself for proper operation, program the UART for baud rate, byte stop, etc., and perform other conventional housekeeping functions required by a microprocessor such as the CPU 60 upon start up. Next, a decision block step 204 determines whether the ACS 10 is in scan mode or program mode. This is determined by one byte in a nonvolatile memory location, which is set for one if scan mode and zero if not. To exit the scan mode, a therapist only need hook up the smart terminal 24, type in a "A" for "abort", and the ACS 10 software will recognize that it should enter the program mode.

When in the scan mode the ACS 10 takes three steps whenever the switch is polled for status as part of the initial scan routine, step 206. These three steps are:
(1) check for low voltage condition on the power supply module 12, and shut down if a low power condition is detected; (2) check the RS232 port for the letter "A" to determine whether to enter program mode; and (3) check the status of the single switch 48 and respond appropriately if in scan mode. Scan mode will be described further in connection with FIG. 6.

If, as determined at decision diamond 204, the system is in the program mode, the ACS 10 first displays operating system headings on the smart terminal 24 as indicated in block 208 in FIG. 4. These headings are the same headings that are displayed when the "QUERY" command is activated as explained above. Next, the external communications module 18 is queried to determine if there is any input from the keyboard of the smart terminal 24, as shown in block 210. Basically, the software will wait until such an input is received. Once an input is received the software flow proceeds to check for an end of line (EOL) character, as shown in decision diamond 212. If the character just received from the RS232 interface is not an end of line character, the character just received is added to the input buffer maintained within system RAM 66, as shown in block 214. The software then returns to block 210 via flow path 216. If the end of line character is received, as determined by diamond 212, the software processes the input buffer as indicated in block 218 and proceeds to decision diamond 220 shown in FIG. 5 where the input buffer is checked to see if it is empty. If the input buffer is empty, the software displays a prompt on the CRT of terminal 24 and resets the input buffer, as shown in block 222, and returns via flow path 224 to block 210. If the input buffer is not empty, the system 10 first determines if the information in the next input buffer has a line number as indicated by decision diamond 226. If no the information within the input buffer must be a system command, which is therefore executed as indicated by block 228. The system then returns to decision diamond 204 via path 229.

If at diamond 226 the input buffer does contain a line number, the software flow proceeds to decision diamond 232, where the input buffer is checked to see whether a scan list exists therein. This is done by looking for the colon. If the scan list does not exist, the software then causes the text within the input buffer to be spoken as shown in block 234. If a semicolon is found to exist within the information in the input buffer, the phonological representation of the text (which is normally a word or phrase) is spoken. If the input buffer does not contain a semicolon, the orthographic representation of the word is spoken. The software then returns to block 210 via path 235.

The pronunciation of any given word within a text line in the user program, is achieved by use of conventional software which converts the English language spelling of the word (or phrase) to its phoneme pronunciation. A suitable or conventional type of English spelling to phoneme translation software may be used, such as software based upon the Naval Research Laboratory Text-to-phoneme Rules. One specific example of such software is provided in the microfiche appendix. Basically, this software simply takes English language text available in ASCII code from the input buffer and parses it to produce a phoneme-based representation which is output in parallel by the microcomputer 16 to the Votrax SCO1 chip 108 in the voice module 20 as shown in FIG. 2. The specific manner in which the Votrax SCO1 chip 108 is driven or controlled by input data is described in Votrax user catalogs available from Votrax, Inc. and thus need not be discussed here.

If the input buffer did contain a scan list as determined at decision diamond 232 of FIG. 5, by the presence of a colon, program control proceeds to block 240 which parses the input buffer contents. This parsing operation performs the following functions. First, the location of the comma, the semicolon and the colon are determined within the input line in the input buffer. Next, all line numbers are compressed into two-digit binary values and stored in scratch pad memory within RAM in module 66. During this time, the line numbers are checked for acceptable ranges. This is done by determining if the line is greater than zero and less than 65,536. Next, the prefix codes are checked to make sure they fall within one of the allowed entries as previously described for the TSLI syntax. An error code is given on the CRT if the prefix code is not one of the allowed letters in the syntax table. Other normal error checking is also done. For example, if the colon exists, a line number must be displayed thereafter or else a suitable error message will be displayed upon the CRT.

These error checking steps are represented in FIG. 5 by the decision diamond 242; and the display of the error messages is shown in block 244. The existence of an error in the parsed input line causes the input buffer to be reset as shown in block 244, and program control then returns via path 224 to block 210.

If no errors are detected in the input line just parsed, program control proceeds to block 250. At block 250, the input line just received is inserted into the appropriate portion of the user text area. This is accomplished by the operating system checking the string of sequential line numbers, determining where this new line to be added should be inserted, and necessary shifting down the remaining text in lines having lower line numbers by an appropriate number of bytes to allow insertion of this line number. This particular scheme for handling storage of the users program is particularly efficient, since it does not involve the use of any unnecessary pointers or the need to periodically run garbage collection routines to compress a file, as is necessary with indexed file structures.

Once the new line of text has been appropriately inserted into the user text area, the input buffer is reset in block 252 and program control returns via line 224 to block 210 to look for the next character input from the smart terminal keyboard 24.

Once all of the desired program changes have been made, the programmer types in the system command "run". The lack of a line number is detected a decision diamond 226 and executed at block 228, causing the system to return to decision diamond 204 and to the scan or user mode via block 206. Once this happens, the operating system turns control over to the interpreter which begins executing the user program stored in nonvolatile memory in block 66 (see FIG. 2) at a predetermined address.

The operation of the ACS software, when in the user mode, is shown in the flow chart in FIG. 6. When the system 10 is in the scan or user mode as determined by the system command "run" executed in block 228, shown in FIG. 5, and also as determined by decision diamond 204 shown in FIG. 4, the initial scan routines in block 206 are performed. When the user switch 48 is actuated for a period of time less than the time determined by the "wait" system command, the system will begin at the first line of the program, as shown in block 260 in FIG. 6. Alternatively, if the user switch 48 is actuated for at least the time determined by the "wait" command, the program will begin block 260 at the second line and will enter the control level. Whether in the start level or the control level the system proceeds to decision diamond 262 and determines whether there is more than one line number in the list following the colon in the current line. If there is only one line number, as shown in box 263, the system 10 will execute the prefix code of the current line and proceed to the single line number following the colon. The system will then return to decision diamond 262 via path 264. Where decision diamond 262 determines that there is more than one line number in the list the system will speak the first line number in the scan vector through the private speaker 28 as indicated by block 266.

Next, as indicated in decision diamond 268, ACS 10 determines if the user has actuated the user switch 48. If not, the software determines at decision diamond 270 if the switch closure monitor time specified by the "scan" command has expired. If this time has not expired, the software proceeds along path 272 back to decision diamond 268 and continues to look for a switch closure until the switch monitor time is over. If no switch closure is detected within the switch monitor time, block 274 sets the pointer for the next line number in the scan vector. Then, at decision block 276 ACS 10 determines whether the maximum number of cycles has been reached as set by the "auto" command. If the maximum number of cycles has not been reached, the software proceeds via path 278 back to block 266 and the next referenced line in the scan vector is spoken through the private speaker. In this way each referenced line in the scan vector of the current line will be spoken in turn, and this cycle will be repeated, until a switch closure is made or the maximum number of cycles is reached. When the maximum number of cycles is reached without a switch closure, the system 10 will turn itself off as shown in block 280. This will save battery power in those instances when the system is left on and unattended.

If a switch closure is detected at decision diamond 268, block 282 will execute the prefix code of the line number currently being spoken by block 266. For example, if the numbered line being spoken had a prefix code of "V", the particular word in that line will be selected and placed into the text buffer. The software then proceeds via path 284 to the decision diamond 262 which operates on the line number following the colon in the line just executed.

E. EXAMPLES OF SYSTEM OPERATION

1. Generating Sentences

To generate sentences the user first selects a category. A sample TSLI program line may be as follows:
1500 C,PLACES;pLAYCIZ:1510:1520:1530
The line numbers which follow the colon direct the scanning. The words found at these line numbers are then heard after the "places" category is selected. A sample program using the selected "places" category line may be as follows:
1500 C,PLACES;PLAYCIZ:1510:1520:1530
1510 V,SCHOOL;SCHOOL:1000
1520 V,MOVIES;MOOVEEZ:1000
1530 V,OUTSIDE;OUTT SIGHDE:1000

If the category "places" is selected by the user via switch activation, the numbers following the phonetic spelling direct the ACS 10 to automatically scan (auditorily scroll through) line numbers 1510, 1520, 1530. The user hears: "school", "movies" and "outside" until one vocabulary word is selected. The cycle of these three words will be repeated until a selection is made. The line number 1000 was arbitrarily selected for this example; this tells the ACS 10 where to go next in the database once the selected word has been stored in the buffer or spoken out. Individual items (words or phrases) should generally not exceed ten to avoid a long list that the user must scan through. If there are too many words for one category it is best to subcategorize as shown in the following sample program:
3000 C,FOOD;FOO DD:3010:3060:3120
3010 C,DRINKS;DDREENKCE:3020:3030:3040:3050
  3020
  3030
  3040
  3050
3060                             C,SNACKS;SNAAHKCE:3070:3080:3090:3100:3110
  3070
  3080
  3090
  3100
  3110
3120 C,BREAKFAST;BRECKFIST:3130:3140:3150
  3130
  3140
  3150

In this sample program, different types of drinks would be presented via lines 3020 to 3050, different types of snacks would be presented in lines 3070 to 3110, and different types of breakfast foods would be presented via lines 3130–3150.

2. Wheel Chair Control

The mobility program for wheel chair control can be used as an isolated program within the system 10, or it can be used as a supercategory as part of a database containing other useful programs. Such other programs might include a vocabulary program as well as ones for the Windsford feeder and environmental controls.

A typical mobility program contains at least the following four lines (in this example, lines-1010, 1020, 1030 and 1040):
1000 C,START:1010:1020:1030:1040
1010 W,FOREWARD;FORWURDD:1000
1020 X,RIGHT;RITTE:1000
1030 Y,LEFT;LEFTT:1000
1040 Z,BACK;BAAHKK:1000

When any direction is selected, the auditory scanning stops as the wheel chair continues to move in that direction until the switch is contacted again. The chair stops and the auditory scroll begins again.

In this example, line 1000 indicates the beginning of the mobility program. This initial line would naturally have different line numbers if the mobility program were part of a larger database. It should be noted that any label could be used which the user would hear through the private speaker 28: "wheelchair", "drive wheelchair" and "mobility" are examples, but it could be labelled anything which was meaningful to the user. The directions will be heard through the private speaker 28 only. It is important that: 1) the four directions are each given a separate line number; 2) the initial program line scans through all four directions; 3) each direction line in the program loops back to the initial line in order to continue scanning within the category; and 4) the code letters W,X,Y,Z are used since these functions are similar to the way that the four separate switches on conventional controls for power wheelchairs function.

The exact order of the directions presented can vary if a different order works best for the individual. However, the direction programmed after a certain letter must have its corresponding jack (jacks are labelled W,X,Y, or Z) inserted into the matching directional receiving part on the power chair. For example, if "X" is programmed for "back", the jack from the relay cable labelled "X" must be inserted into the plug for the reverse control on the power chair.

The exact words chosen to represent each direction can be individualized. An adult may want the word "reverse" while "back", "go back" or "backwards" may be appropriate for younger people.

It is also useful to add at least one more line to the mobility program which will allow the user to: 1) turn the ACS 10 off; or 2) escape from the wheelchair program to another desirable part of the database, often the beginning. Any word to signal stopping the program for mobility can be used such as "stop" or "quit". An example of such a program follows.
2100 C,WHEELCHAIR;2110:2120:2130:2140:2150
2110 W,FOREWARD:FORWURDD:2100F
2120 X,RIGHT;RITTE:2100
2130 Y,LEFT;LEFTT:2100
2140 Z,BACK;BAAHKK:2100
2150 C,QUIT;KWITT:1000

Note: line 2150 is given the "C" command so that it will be heard through the private speaker 24, and not the public speaker 30; if selected via switch activation, the program automatically goes to the line number indicated.

F. ADDITIONAL FEATURES AND ENHANCEMENTS

Besides controlling a wheelchair as illustrated in the above example, the ACS 10 may be used to control additional external devices. As mentioned above, the relay contacts 106a-106d may be used to control a Windsford feeder. In addition, the four contacts may also be used to control between one and four toys. Typically, the selection between the external devices to be driven will be made by plugging and unplugging an individual cable into the ACS 10 to couple the external device to the relay contacts 106a-106d. Where it is desired to control more than one external device without plugging and unplugging, it will be appreciated by those skilled in the art that the ACS 10 could be provided with more than four outputs and a conventional multiplexing technique could be used to send appropriate signals to different external devices which could all be plugged in at the same time. Thus there is nothing to prevent the user from controlling an external device and also carrying on a conversation.

Another external device which can be controlled by the ACS 10 is the General Electric Home Minder system which utilizes a conventional infrared control interface housed in a hand-holdable remote control package. Basically, the Home Minder system is an entertainment and home environment control center which includes a color television with remote control channel selection that is accomplished via the interface in the same manner as normal television remote control devices. The Home Minder system also can be connected to and has the capability of turning on through its remote control device appliance modules within the home which are part of the system. For example, the furnace/air conditioning (A/C) system of the home can be connected to a control module of the Home Minder system, and then the furnace or A/C turned on and off and temperatures set. Lights within the house can be similarly connected and then turned on and off, as well as dimmed or raised. This particular environmental system is just one example of the kinds of controls which the ACS 10 can be adapted to interface with. The particular circuit for the infrared control interface (shown as block 40 in FIG. 2) which is used, is not deemed to constitute part of the present invention, since the circuit will vary depending upon which brand of infrared remote control device is being connected to the ACS 10.

G. EPILOGUE

The methods and systems of the present invention introduce basic functional concepts for single switch augmentive communication technology for handicapped individuals, and an architectural framework for implementing that technology using an interpreter and a simplified programming language. Accordingly, those skilled in the art will appreciate that the methods and systems of our preferred embodiments are well-suited to achieve the objects above-stated. It is recognized that those skilled in the art may make various modifications or additions to the preferred embodiments chosen to illustrate the invention without departing from the spirit and the scope of the present contribution to the art. For example, where the user has special requirements a single switch may be adapted to be activated in a number of unique ways such as by very slight motion of any part of the user's body. Also, depending on a given user's particular handicaps, the presentation of choices may be by visual means such as a printer instead of the private speaker 28. Likewise, in some cases it may be desirable to substitute a CRT or flat panel display in place of the public speaker 30. Also, the TSLI language used with the ACS 10 provides the means to permit the user to preprogram selected words or phrases for a particular social setting that the user finds himself in. For example, a user may wish to preprogram messages in preparation for a trip to a particular person's house, or to program a set of responses to particular homework assignments for a classroom setting.

Finally, it should be recognized that the number of relay outputs 106a-106d may be increased so that the ACS 10 may be wired to several types of devices at the same time, and/or to provide control signals of complex external devices such as a computer. Thus, those skilled in the art will appreciate that the ACS 10 may be used to provide a kind of substitute keyboard to permit the user to interface with the computer by actuating a selected number of the keys on a computer keyboard in sequence, or in combination, by using if needed the ACS input buffer to hold the desired key strokes until an assembled string of key strokes is ready to be sent to the external computer. Accordingly, it is to be understood that the present invention is not limited to the specific embodiments chosen to illustrate the invention herein, but should be deemed to the extend to the subject matter defined by the amended claims, including all fair equivalents thereof.

We claim:

1. In a programmable system for enabling a user to generate sentences from a set of stored words and phrases by actuating a single switch in response to choices presented to said user, a method of generating said sentences in said system comprising the steps of:

storing in said programmable system at least one set of numbered instructions executable by said system which defines said choices and their order of presentation, said set of instructions including individually numbered instructions, each having a first line number for identification, a command symbol, at least one word to be presented to said user as one of said choices, and at least one second line number for indicating which individual instruction to execute next;

executing said instructions in said system by:
(a) locating a first individual instruction to be executed from the set of instructions;
(b) determining if there is more than one second line number in the instruction to be executed;
(c) when there is no more than one second line number in the instruction to be executed, executing the function defined by the command symbol of the instruction to be executed, and proceeding to the individual instruction indicated by the second line number designated in the instruction to be executed;
(d) when there is more than one second line number in the instruction to be executed, presenting a word in an individual instruction indicated by the first such second line number to said user;
(e) determining if said single switch has been actuated within a predetermined interval of time after said word is presented to said user;
(f) when said switch is actuated within said predetermined interval of time, executing a function defined by a command symbol in the individual instruction indicated by the first such second line in the instruction to be executed, and proceeding to the next second line number designated in the instruction to be executed;

(g) when said switch is not activated within said predetermined interval of time, presenting to said user a word in another individual instruction indicated by the next second line number in the instruction to be executed; and (h) repeating steps (e), (f), and (g) for each successive second line number listed in the instruction to be executed.

2. A method of generating sentences as in claim 1 and in which the programmable system includes a message buffer, wherein one of said command symbols will cause said system to add said word in the line to said message buffer.

3. A method of generating sentences as in claim 2 further comprising the steps of:

determining when the length of time said switch is actuated falls within a predetermined range;

when said length of time is within said predetermined range, presenting said user with control choices which, when chosen, will cause said system to form one of a plurality of steps including the steps of:

presenting the word in said message buffer to said user; and presenting the word in said message buffer to a person other than said user.

4. A method of generating sentences as in claim 3 wherein said control choices further include choices which:

cause said system to remove the previous word from said message buffer;

remove all the words from the message buffer; and turn the system off.

5. A method of generating sentences as in claim 3 wherein:

said control choices further include choices which cause said system to activate at least one of a plurality of relays, said relays being connected to external devices.

6. A method of generating sentences as in claim 1 further comprising the steps of:

providing a first speaker which is in close proximity to said user wherein said speaker will be heard primarily by said user; and step (d) further comprises the step of transmitting an audio speech signal representative of said word to said first speaker.

7. A method of generating sentences as in claim 3 further comprising the steps of:

providing a second speaker which is easily heard by a person other than said user, and wherein said step of presenting said word in said message buffer to a person other than said user further includes the step of transmitting a speech signal representative of said word stored in said buffer to said second speaker.

8. A programmable system for enabling a user to generate sentences from a set of stored words and phrases by actuating a single switch in response to choices presented to said user, said system comprising:

means for storing in said system a set of instructions executable by said system, which defines said choices and their order of presentation, said set of instructions including individual instructions, each having a first line number for identification, a command symbol, at least one word to be presented to said user as one of said choices, and at least one second line number for indicating which line to execute next;

means for executing said instructions in said system including:

(a) means for locating a first instruction line within the set of instructions;

(b) means for determining if there are more than two second line numbers in an instruction;

(c) means for executing a function defined by a command symbol in an instruction;

(d) means for presenting a word includes in an instruction to said user;

(e) means for determining if said single switch has been actuated within a predetermined interval of time after a word is presented to said user; and (f) means for executing a function defined by a command symbol in an instruction; and (g) means for proceeding to another instruction indicated by a second line number in an instruction currently being executed.

9. A system as in claim 8 further comprising:

an message buffer; and means responsive to one of said command symbols for causing said system to add a word in an instruction designated by a second line number in an instruction currently being executed to said message buffer.

10. A system of generating sentences as in claim 9 further comprising:

means for determining whether said switch is actuated for more than a predetermined length of time;

means for presenting said switch is actuated for more than a predetermined length of time;

means for presenting said user with control choices;

means for selectively presenting words added to said message buffer to said user; and means for selectively presenting words added to said message buffer to a person other than said user.

11. A system as in claim 10 further comprising:

means for causing said system to remove a word previously added to said message buffer from said message buffer; and means for removing all the words from the message buffer substantially at 12. A system as in claim 8 further comprising:

a plurality of relays connectable to an external device having a plurality of controllable functions; and means responsive to said control choices for causing said system to activate selectively at least one of said plurality of relays, whereby said user can actively control said controllable functions of said external device using said single switch when said system is connected thereto.

13. A system as in claim 8 further comprising:

a first speaker which is in proximity to said user such that said speaker will be heard primarily by said user; and means for transmitting an audio speech signal representative of said word to said first speaker.

14. A system as in claim 8, wherein said means for executing said instructions includes an interpreter program, and wherein said individual instructions form part of a simplified computer language easily learned by persons without experience in computer programming.

* * * * *

UNITED STATES PATENT AND TRADEMARK OFFICE
CERTIFICATE OF CORRECTION

PATENT NO. : 5,047,953

DATED : September 10, 1991

INVENTOR(S) : Smallwood et al

It is certified that error appears in the above-identified patent and that said Letters Patent is hereby corrected as shown below:

Column 4, line 61, delete "With" and insert ---- with ----.

Column 4, line 64, delete "controllers /buffers" and insert ---- controllers, buffers ----.

Column 8, line 68, delete "the rapist" and insert ---- therapist ----.

Column 9, line 46, delete "(Y.N)" and insert ---- (Y,N) ----.

Column 9, line 60, delete "(Y.N)" and insert ---- (Y,N) ----.

Column 10, line 44, after "SCAN" insert ---- = ----.

Column 10, line 52, delete "(Y.N)" and insert ---- (Y,N) ----.

Column 12, line 54, delete "words," and insert ---- words ----.

Column 17, line 21, delete "C,PLACES;pLAYCIZ:" and insert ---- C,PLACES;PLAYCIZ: ----.

Column 17, line 42, after "out." start a new paragraph.

Column 17, line 53, delete in its entirety.

Column 18, line 54, before "CE" insert ---- 3060 C, SNACKS;SNAAHK ----.

UNITED STATES PATENT AND TRADEMARK OFFICE
CERTIFICATE OF CORRECTION

PATENT NO. : 5,047,953

DATED : September 10, 1991

INVENTOR(S) : Smallwood et al

It is certified that error appears in the above-identified patent and that said Letters Patent is hereby corrected as shown below:

Column 22, line 47, after "at" insert ---- once ----.

Signed and Sealed this

Nineteenth Day of April, 1994

Attest:

BRUCE LEHMAN

*Attesting Officer*   *Commissioner of Patents and Trademarks*